(12) United States Patent
Biscup (10) Patent No.: US 6,689,132 B2
(45) Date of Patent: Feb. 10, 2004

(54) SPINAL IMPLANT INSERTION TOOL

(75) Inventor: Robert S. Biscup, Chagrin Falls, OH (US)

(73) Assignee: Spineco, Inc., Avon, OH (US)

( * ) Notice: Subject to any disclaimer, the term of this patent is extended or adjusted under 35 U.S.C. 154(b) by 0 days.

(21) Appl. No.: 10/274,460

(22) Filed: Oct. 18, 2002

(65) Prior Publication Data

US 2003/0216737 A1 Nov. 20, 2003

Related U.S. Application Data

(60) Provisional application No. 60/380,479, filed on May 15, 2002.

(51) Int. Cl.[7] ............................................... A61B 17/70
(52) U.S. Cl. ........................................... 606/61; 606/99
(58) Field of Search ............................. 606/53, 60, 61, 606/86, 96, 99, 102, 190; 623/17.11–17.16

(56) References Cited

U.S. PATENT DOCUMENTS

| | | |
|---|---|---|
| 4,349,921 A | 9/1982 | Kuntz |
| 4,714,469 A | 12/1987 | Kenna |
| 4,834,757 A | 5/1989 | Brantigan |
| 4,878,915 A | 11/1989 | Brantigan |
| 4,934,848 A | 6/1990 | Hayashi et al. |
| 4,961,740 A | 10/1990 | Ray et al. |
| 5,192,327 A | 3/1993 | Brantigan |
| D374,283 S | 10/1996 | Michelson |
| 6,159,215 A | 12/2000 | Urbahns et al. |
| 6,270,498 B1 | 8/2001 | Michelson |
| 6,428,544 B1 * | 8/2002 | Ralph et al. .................. 606/99 |
| 2002/0019637 A1 * | 2/2002 | Frey et al. .................... 606/85 |

* cited by examiner

*Primary Examiner*—David O. Reip
(74) *Attorney, Agent, or Firm*—Fay, Sharpe, Fagan, Minnich & McKee

(57) ABSTRACT

An insertion tool to guide and/or insert an implant into an intervertebral disc space. The insertion tool includes a body member and a curvilinear top portion connected to the body member. The top portion has a total angle of curvature of at least about 90° and a size and shape to enable over 50% of the top portion to be positioned within an outer perimeter of the intervertebral disc space.

70 Claims, 7 Drawing Sheets

SPINAL IMPLANT INSERTION TOOL

This patent application claims priority on co-pending U.S. Provisional Patent Application Serial No. 60/380,479 filed May 15, 2002 entitled "Intervertebral and Intravertebral Disc Implant Guide Device and Methodology". The present invention pertains to prosthetic devices and, more particularly, to instrumentation for facilitating in the guiding and/or inserting prosthetic devices between two or more vertebrae.

INCORPORATION BY REFERENCE

U.S. Provisional Application Serial No. 60/380,479 filed May 15, 2002 is incorporated herein by reference. U.S. Pat. Nos. 6,270,498; 6,159,215, and Des. 374,283 are also incorporated herein by reference to provide background information on prior art devices for inserting components between two vertebrae.

BACKGROUND OF THE INVENTION

The human spine is made up of a column of thirty-three bones and their adjoining structures. The bodies of these vertebrae are connected by anterior and posterior ligaments and by discs of fibrocartilage generally known as intervertebral discs. These discs are positioned between opposite faces of adjacent vertebral bodies. This column of vertebrae and intervertebral discs form a central axis that supports the head and torso. These vertebrae also enclose an opening through which the spinal cord passes.

The presacral vertebrae are normally held in position to one another by the intervertebral discs, ligaments and musculature of the body. These vertebrae move relative to adjacent vertebrae thus permitting the head to be turned relative the body and providing a wide range of flexibility to the spine.

One of the most costly health problems in society involves back pain and pathology of the spine. These problems can affect individuals of all ages and can result in great suffering to victims. Back pain can be caused by several factors such as congenital deformities, traumatic injuries, degenerative changes to the spine, and the like. Such changes can cause painful excessive motion, or collapse of a motion segment resulting in the contraction of the spinal canal and compression of the neural structures, causing debilitating pain, paralysis or both, which in turn can result in nerve root compression or spinal stenosis.

Nerve conduction disorders can also be associated with intervertebral discs or the vertebrae themselves. One such condition is herniation of the intervertebral disc, in which a small amount of tissue protrudes from the sides of the disc into the foramen to compress the spinal cord. A second common condition involves the development of small bone spurs, termed osteophytes, along the posterior surface of the vertebral body, again impinging on the spinal cord.

Upon identification of these abnormalities, surgery may be required to correct the problem. For those problems associated with the formation of osteophytes or herniations of the intervertebral disc, one such surgical procedure is intervertebral discectomy. In this procedure, the involved vertebrae are exposed and the intervertebral disc is removed, thus removing the offending tissue or providing access for the removal of the bone osteophytes. A second procedure, termed a spinal fusion, may then be required to fix the vertebrae together to prevent movement and maintain a space originally occupied by the intervertebral disc. Although this procedure may result in some minor loss and flexibility in the spine, due to the relatively large number of vertebrae, the minor loss of mobility is typically acceptable.

During an intervertebral discectomy, a prosthetic implant or spinal implant is inserted in the vertebral disc space. This prosthetic implant is often a bone graft removed from another portion of the patient's body, termed an autograft. The use of bone taken from a patient's body has the important advantage of avoiding rejection of the implant, but has several shortcomings. There is also a risk of opening a second surgical site to obtain the implant, which can lead to infection or pain for the patient, and the second surgical site is weakened by the removal of material. The bone implant may also not be perfectly shaped for placement between the vertebrae, thus leading to slippage or absorption of the implant, or failure of the implant to fuse with the vertebrae.

Other options for a graft source of implant are bone removal removed from cadavers, termed allograft, or from other species, termed a xenograft. In these cases, while there is the benefit of not having a second surgical site, thus reducing the incidence of infection or pain at such second site, there is increased difficulty associated with graft rejection and the risk of transmitting communicable diseases.

An alternative approach to using a bone graft is using a manufactured implant made of synthetic material which is biologically compatible with the body and the vertebrae. Several compositions and geometries of such implants have been utilized, ranging from simple blocks of material to carefully shaped implants, with varying success.

There has been an extensive number of attempts to develop an acceptable prosthetic implant that can be used to replace an intervertebral disc and yet maintain the stability of the intervertebral disc space between adjacent vertebrae, at least until complete arthrodesis is achieved. For fusion to occur between the prosthetic implants, it is typically necessary to prepare the vertebrae to be fused by breaking through or cutting into the hardened outside plates of the bone to allow the interposed bone graft to come into direct contact with the prosthetic implant, thereby tricking the body into attempting to heal itself and to bond with the prosthetic implant. While many types of synthetic prosthetic devices have been proposed, the success rates have been low and the surgical procedures have been complicated and often traumatic to the patient.

One of the more prevailing designs of these prosthetic implants takes the form of a cylindrical implant. These types of prosthetic implants are represented by Brantigan U.S. Pat. No. 4,878,915 and Ray U.S. Pat. No. 4,961,740, which are incorporated herein by reference. In these cylindrical implants, the exterior portion of the cylinder can be threaded to facilitate insertion of the prosthetic device. Some of these prosthetic implants are designed to be pounded into the intervertebral disc space. These types of devices are represented in Brantigan U.S. Pat. No. 4,834,757 and Brantigan U.S. Pat. No. 5,192,327, which are incorporated herein by reference. The Brantigan and Ray patents disclose prosthetic implants wherein the transverse cross-section of the implant is constant throughout the length of the implant, and is typically in the formed of a circular cylinder.

Other prosthetic implants have been developed that do not have a constant cross-section. For instance, the patent to McKinna U.S. Pat. No. 4,714,469 illustrates a spherical implant with elongated protuberances that project into the vertebral end plate. The implant of Bagby U.S. Pat. No. 4,934,848 is in the form of a sphere which is positioned between the centrums of the adjacent vertebrae. Both of these disclosures are incorporated herein by reference.

Various prosthetic implants can be generally divided into two basic categories, namely solid implants and implants designed to encourage bone growth. Solid implants are represented by U.S. Pat. Nos. 4,878,915 and 4,349,921, which are incorporated herein by reference. The other patents discussed above permit bone to grow across and/or into the implant. It has been found that devices which promote natural bone growth achieve a more rapid and stable arthrodesis. These implants are typically filled with autologous bone prior to insertion into the intervertebral disc space. These implants typically include apertures which communicate with openings in the implant, thereby providing a path for tissue growth between the vertebral end plate and the bone or bone substitute within the implant.

A number of difficulties remain with the use of these prior art prosthetic implants. While it is recognized that hollow implants which promote bone growth into the implant is an optimal technique for achieving fusion, most of these devices have difficulty achieving this fusion, at least without the aid of some additional stabilizing device, such as a rod or plate. Moreover, some of these devices are not structurally strong enough to support the heavy loads applied to the most frequently fused vertebral levels, namely those in the lower lumbar spine.

Many of these problems with past prosthetic implants have been overcome by the prosthetic implants disclosed in U.S. patent application Ser. No. 09/865,114 filed May 24, 2001 entitled "Spherical Spinal Implant" and U.S. patent application Ser. No. 09/494,645 filed Jan. 31, 2000 entitled "Spinal Fusion Implant", now U.S. Pat. No. 6,245,108, both of which are incorporated herein by reference. These two patent applications disclose an improved prosthetic implant in the form of a sphere or cage, which implants can permit bone growth with or without the aid of additional devices, and which prosthetic implants are structurally strong to support the heavy loads applied to such implants.

Although many of the past problems with prosthetic devices have been overcome as stated above, there remains a need for a device which facilitates in easily and properly inserting one or more prosthetic implants into the intervertebral disc space while minimizing damage to the spinal cord and/or surrounding tissue. In view of the present state of technology related to prosthetic implants, there is a continued need for new devices and methods to properly and successfully insert prosthetic implants into the intervertebral disc space.

SUMMARY OF THE INVENTION

The present invention relates to prosthetic implants to be placed into the intervertebral disc space, and more particularly, to an apparatus and method for facilitating in the guiding and/or inserting of one or more prosthetic implants into the intervertebral disc space.

In accordance with the principal feature of the present invention, there is provided an insertion tool which can be used with one or more prosthetic implants, which tool is at least partially designed to guide and/or position one or more prosthetic implants into at least a portion of the intervertebral disc space between two adjacent vertebrae. The insertion tool is designed to facilitate the surgical procedure of inserting and/or positioning one or more prosthetic implants between two or more vertebrae, thereby simplifying the surgical procedure. The insertion tool also and/or alternatively facilitates in minimizing or preventing damage to the spinal cord and/or other vital tissue (e.g. large blood vessels, neural structures, muscle, etc.) about the vertebral disk space, thereby minimizing injury and/or complication to the patient during a surgical procedure when inserting one or more prosthetic implants between two or more vertebrae.

In accordance with one aspect of the present invention, there is provided an insertion tool that includes a posterior end portion or top portion which has a shape and/or size that approximates the anterior curve of the intervertebral disc space. In one embodiment of the invention, the posterior end portion of the insertion tool is sized and/or shaped such that at least a majority of the posterior end portion lies within the vertebral annulus (i.e. the ridge at the top/bottom of the vertebrae that matches the border of the spinal discs) when the insertion tool is inserted into the intervertebral disc space. In one aspect of this embodiment, the prosthetic end portion is shaped and/or sized such that at least about 60% of the posterior end portion lies within the annulus when the insertion tool is inserted into the intervertebral disc space. In another and/or alternative aspect of this embodiment, the prosthetic end portion is shaped and/or sized such that at least about 70% of the posterior end portion lies within the annulus when the insertion tool is inserted into the intervertebral disc space. In still another and/or alternative aspect of this embodiment, the prosthetic end portion is shaped and/or sized such that at least about 80% of the posterior end portion lies within the annulus when the insertion tool is inserted into the intervertebral disc space. In yet another and/or alternative aspect of this embodiment, the prosthetic end portion is shaped and/or sized such that at least about 90% of the posterior end portion lies within the annulus when the insertion tool is inserted into the intervertebral disc space. In still yet another and/or alternative aspect of this embodiment, the prosthetic end portion is shaped and/or sized such that substantially all of the posterior end portion lies within the annulus when the insertion tool is inserted into the intervertebral disc space. In another and/or alternative embodiment of the present invention, the posterior end portion is formed of one or more annular or arcuate portions. In one aspect of this embodiment, the posterior end portion is formed by a single arcuate portion of the spinal insert. In one particular configuration of this aspect, the radius of curvature of the arcuate portion is substantially constant throughout the length of the arcuate portion. In another and/or alternative configuration of this aspect, the radius of curvature of the arcuate portion varies at least once along the length of the arcuate portion. In another and/or alternative aspect of this embodiment, the posterior end portion is formed by a plurality of arcuate sections and at least one non-arcuate section. In one particular configuration of this aspect, all the arcuate sections have substantially the same radius of curvature. In another and/or alternative configuration of this aspect, one or more of the arcuate sections have a different radius of curvature from at least one other arcuate section. In still another and/or alternative specific configuration of this aspect, the one or more non-arcuate sections are substantially linear.

In still another and/or alternative aspect of the present invention, the posterior end portion has a total angle of curvature for a particular insertion device which is selected so that the insertion tool can position and/or maintain one or more prosthetic implants in a desired location within the intervertebral disc space. In one embodiment of the invention, the cumulative or total angle of curvature of the posterior end portion is at least about 45°. In one aspect of this embodiment, the total angle of curvature of the posterior end portion is at least about 60°. In another and/or alternative aspect of this embodiment, the total angle of curvature of the posterior end portion is at least about 90°. In still another and/or alternative aspect of this embodiment, the total angle of curvature of the posterior end portion is at least about 120°. In yet another and/or alternative aspect of this embodiment, the total angle of curvature of the posterior end portion is at least about 150°. In still yet another and/or alternative aspect of this embodiment, the total angle of curvature of the posterior end portion is at least about 180°. In yet a further and/or alternative aspect of this embodiment, the total angle of curvature of the posterior end portion is at least about 190°. In still yet a further and/or alternative aspect of this embodiment, the total angle of curvature of the posterior end portion is at least about 200°. In still another and/or alternative aspect of this embodiment, the total angle of curvature of the posterior end portion is at least about 210°. In still yet another and/or alternative aspect of this embodiment, the total angle of curvature of the posterior end portion is at least about 220°.

In yet another and/or alternative aspect of the present invention, the cross-sectional shape and/or size (i.e. thickness) for the posterior end portion of the insertion tool is selected to facilitate in the ease of positioning and/or maintaining one or more prosthetic implants within the intervertebral disc space, to facilitate in the insertion and/or removal of the insertion tool from the intervertebral disc space, to maintain the proper spacing of the intervertebral disc space during the insertion and/or positioning of one or more prosthetic implants within the intervertebral disc space, and/or to minimize damage to surrounding tissue during the insertion and/or positioning of one or more prosthetic implants within the intervertebral disc space. In one embodiment of the invention, the cross-sectional shape and/or size of the prosthetic end portion is substantially constant along the length of the posterior end portion. In another and/or alternative embodiment of the invention, at least a section of the cross-sectional shape and/or size of the posterior end portion is different from another section of the posterior end portion. In still another and/or alternative embodiment of the invention, at least a section of the prosthetic end portion has a substantially circular, square, or rectangular cross-sectional shape. As can be appreciated, other cross-sectional shapes can be used, such as ovoid, polygonal, D-shaped, etc. In yet another and/or alternative embodiment of the invention, the maximum size (i.e. cross-sectional length or diameter) of the prosthetic end portion is less than the minimum space between two adjacent vertebrae that form the intervertebral disc space. Such a thickness of the prosthetic end portion facilitates in the ease of inserting and/or removing the insertion tool from the intervertebral disc space during a surgical procedure. In still yet another and/or alternative embodiment of the invention, at least a section of the posterior end portion has a maximum size which is greater than or equal to the minimum space between two adjacently positioned vertebrae which form the intervertebral disc space. An insertion tool having this design facilitates in at least partially maintaining the spacing between the two adjacent vertebrae so as to facilitate in positioning one or more prosthetic implants into the intervertebral disc space during a surgical procedure. In one aspect of this embodiment, at least a portion of the posterior end portion is expandable and/or contractable, thereby allowing the maximum size of the posterior end portion to be variable. In one non-limiting example, the maximum size of the posterior end portion can be selected to be less than or equal to the minimum space between two adjacent vertebrae to facilitate in the ease of insertion of the insertion tool between two vertebrae. Thereafter, the maximum size can be caused to increase to force apart the two adjacent vertebrae so as to facilitate in the insertion of the implant between the two adjacent vertebrae. After the one or more implants have been properly positioned and/or inserted between the two adjacent vertebrae, the maximum size of the posterior end portion is reduced so that it is less than or equal to the minimum space between the two adjacent vertebrae to facilitate in the removal of the insertion tool from the surgical site. As can be appreciated, the increasing and/or decreasing in the maximum size of one or more portions of the posterior end of the insertion tool can be used in many other manners to facilitate in the positioning and/or insertion of one or more implants between two adjacent vertebrae, and/or to facilitate in the insertion and/or removal of the insertion tool at the surgical site.

In still yet another and/or alternative aspect of the present invention, the insertion tool includes a body portion which is connected to at least one end of the posterior end portion. The body portion is designed to have a sufficient length to allow the surgeon to properly extend the posterior end portion into the intervertebral disc space and/or to maneuver the posterior end portion in the intervertebral disc space during a surgical procedure. In one embodiment of the invention, the body portion is made of a material which is similar to that of the posterior end portion. In another and/or alternative aspect of this embodiment, the body portion is made of one or more materials that are different from the one or more materials forming the posterior end portion. In still another and/or alternative embodiment of the invention, the body portion has a cross-sectional shape and size which is substantially the same as the cross-sectional shape and size of one or more regions of the posterior end portion. In yet another and/or alternative embodiment of the invention, at least a section of the body portion has a cross-sectional size and/or shape that is different from one or more regions of the posterior end portion. In still yet another and/or alternative embodiment of the invention, the body portion includes one or more substantially straight or linear regions. In one aspect of this embodiment, at least a majority of the body portion is substantially straight or linear. As can be appreciated, the body portion can have other shapes and/or sizes depending on the desired end use of the insertion tool and/or the end use of the body portion of the insertion tool. In a further and/or alternative embodiment of the invention, the body portion is about 2–10 inches in length; however, other lengths can be used.

In another and/or alternative aspect of the present invention, the insertion tool includes a lower or base portion that is at least partially designed to facilitate in gripping the insertion tool during use. In one embodiment, the base portion includes one or more arcuate portions. In one aspect of this embodiment of the invention, the arcuate portions create an S-shaped look to the insertion tool. In another and/or alternative aspect of the embodiment, the arcuate sections of the base portion create a C-shaped look to the insertion tool. In still another and/or alternative aspect of this embodiment, the base portion is formed by a single arcuate section. In one specific configuration of this aspect, the radius of curvature of the single arcuate section is substantially constant. In another and/or alternative specific configuration of this aspect, the radius of curvature varies at least along one section of the arcuate section of the base portion. In still yet another and/or alternative aspect of this embodiment, the base portion is formed by a plurality of arcuate sections and at least one non-arcuate section. In one specific configuration of this aspect, the radius of curvature of the plurality of arcuate sections is substantially the same. In another and/or alternative specific configuration of this aspect, at least one of the arcuate sections has a different radius of curvature than another of the arcuate sections. In still another and/or alternative specific configuration of this aspect, at least one of the non-arcuate sections of the base portion is substantially straight or linear. In still yet another embodiment of the invention, the cross-sectional shape and/or size of the base portion is substantially constant. In a further and/or alternative aspect of this embodiment, at least one section of the base portion has a different cross-sectional shape and/or area than at least one other section of the base portion. In still a further and/or alternative embodiment of the invention, the base portion is made of a material which is substantially the same as the body portion of the insertion tool. In yet a further and/or alternative embodiment of the invention, at least a section of the base portion includes a material which is different from at least a section of the body portion of the insertion tool. In yet another and/or alternative embodiment of this invention, the curvature of the base portion lies in substantially the same plane as the curvature of the posterior end portion of the insertion tool. In a further and/or alternative embodiment of the present invention, at least a portion of the curvature of the base portion lies in a plane which is different from the plane in which at least a portion of the posterior end portion lies. In still a further embodiment of the present invention, the base section is substantially linear or straight. In yet a further and/or alternative embodiment of this invention, the base portion includes at least one gripping element. In one aspect of this embodiment, the gripping element includes, but are not limited to, ribs, grooves, slots, openings, ridges, pits, corrugations, etc. The gripping element is designed to facilitate in maintaining a grip by the surgeon on the base portion when using the insertion tool. In another and/or alternative aspect of this embodiment, the gripping element includes one or more coatings of a material (e.g. plastic, polymers, etc.) to facilitate in handling the insertion tool during use.

In still another and/or alternative aspect of the present invention, the insertion tool includes one or more smooth surfaces designed to reduce or eliminate damage to surrounding tissue when the insertion tool is inserted, positioned and/or removed from an intervertebral disc space during a surgical procedure. In one embodiment of the invention, the posterior end portion includes one or more smooth surfaces. In one aspect of this embodiment, the outer surface of the posterior end portion is substantially smooth. In another and/or alternative aspect of this embodiment, the inner surface of the posterior end portion is substantially smooth. In still another and/or alternative aspect of this embodiment, the end of the posterior end portion is substantially smooth. In another embodiment of this invention, one or more sections of the body portion of the insertion tool are substantially smooth. In still yet another and/or alternative embodiment of the present invention, one or more sections of the base portion are substantially smooth. In a further and/or alternative embodiment of the present invention, one or more sections of the insertion tool are smoothed by various mechanical means such as, but not limited to, sanding, grinding, polishing, and/or the like. In still a further and/or alternative embodiment of the present invention, one or more surfaces of the insertion tool are smoothed by coating such surfaces to form a substantially smooth surface. Such materials can include, but are not limited to, various types of plastics, polymers, metal plating and the like.

In yet another and/or alternative aspect of the present invention, the insertion tool is made of a biocompatible and/or durable material. The material selected for the insertion tool should be biocompatible, so as not to cause irritation, infection, or other complications during a surgical procedure. The material used for the insertion tool should also be durable enough so that the insertion tool can successfully accomplish at least one of the surgical procedures for which the insertion tool is design. In one embodiment of the invention, the insertion tool includes stainless steel, titanium, chromemolybdenum, cobalt chromium alloy, chrome or chrome alloys, cobalt or cobalt alloys, ceramic (i.e. xirconium oxide ceramic, aluminum oxide ceramic, etc.), and/or polymers (i.e. polycarbonate, polypropylene, polyethylene, polymethylmethacrylate, polysolfone, polymers filled with glass and/or carbon fibers, various types of carbons and/or fiber reinforced polymers, plastic, etc.). In still another and/or alternative embodiment of the invention, the material used to at least partially form the insertion tool is substantially a rigid material; thus, the insertion tool resists any type of deformation during use. In still yet another and/or alternative embodiment of the invention, at least a portion of the insertion tool includes a flexible or semi-flexible material which provides some flexibility to the insertion tool during use. In a further and/or alternative embodiment of the invention, the insertion tool is formed of a material which can be sterilized at least once prior to use. In one aspect of this embodiment, the insertion tool is formed of a material which can be sterilized multiple times for multiple uses.

In yet another and/or alternative aspect of the present invention, the base portion of the insertion tool is configured so as to maintain and/or position one or more spinal implants in an intervertebral disc space. In such a configuration, the posterior end portion and/or the base portion can be used to partially or fully insert a prosthetic implant in the intervertebral disc space. When the base portion is configured for such use, typically, the size and/or shape of the base portion is different from the size and/or shape of the posterior end portion. The total angle of curvature of the base portion can be the same and/or different than the total angle of curvature of the posterior end portion.

In a further and/or alternative aspect of the present invention, multiple insertion tools are used by the surgeon wherein the posterior end portion of one or more of the multiple insertion tools is different from one or more of the posterior end portions of one or more other insertion tools. The use of a set of differently configured insertion tools allows a surgeon to select the appropriate insertion tool that can be best used on a particular patient. Due to the age, height, and/or build of a patient, the intervertebral disc space of a particular patient will differ from patient to patient, thus different sized and/or shaped insertion tools can be used to accommodate the specific physiology of a particular patient.

In still a further and/or alternative embodiment of the present invention, at least a portion of the insertion tool is coated with a material which facilitates in the success of the surgical procedure involving the use of a prosthetic implant. In one embodiment of this invention, the substance includes a material that facilitates in the formation of a graft between one or more vertebrae. In one aspect of this embodiment, the substance includes, but is not limited to, medicine, human tissue, animal tissue, synthetic tissue, human cells, animal cells, synthetic cells, and the like. In another and/or alternative embodiment of the invention, at least one of the substances includes, but is not limited to, a compound that promotes bone or other tissue growth which inhibits rejection of the prosthetic implants, reduces infection, reduces inflammation, reduces pain, promotes healing of surrounding tissue, functions as a locator and/or visual indicator, and the like. In still another and/or alternative embodiment of the invention, the coating material is designed to at least partially control or regulate the release of one or more substances coated on and/or contained within the insertion tool.

In yet a further and/or alternative embodiment of the present invention, the insertion tool includes one or more guide arrangements designed to at least partially guide one or more prosthetic implants, and/or one or more other materials and/or devices into the interior region of the posterior end portion. In one embodiment of the invention, the guide arrangement includes at least one slot and/or groove positioned on at least a portion of the interior surface of the posterior end portion. When such a slot or groove is used, the prosthetic implant and/or other device includes a corresponding structure that is designed to engage the groove and/or slot so as to be at least partially guided by the groove or slot. As can be appreciated, other types of guide arrangements can be used, such as ridges, ribs, and the like. In another and/or alternative embodiment of the invention, the guide mechanism includes one or more movable carriages to which one or more implants can be connected to and/or released therefrom. In one aspect of this embodiment, an implant is connected to a movable carriage and the movable carriage moves the implant at least partially along and/or within the interior region of the posterior end portion. The guide arrangement can include a releaseable connection to release the implant once the implant is properly positioned. In still another and/or alternative embodiment of the present invention, at least one guide arrangement travels substantially along the full interior surface length of the posterior end portion. In another and/or alternative embodiment of the present invention, the guide arrangement is positioned along a portion of the interior surface of the posterior end portion. In still yet another and/or alternative embodiment of the present invention, one or more guide arrangements are positioned on the outer surface of the posterior end portion.

In still yet a further and/or alternative aspect of the present invention, the insertion tool includes one or more side passageways which provide access to the interior region of the posterior end portion during a surgical procedure. The side passageway can be designed to allow materials to be inserted into and/or removed from the interior region of the posterior end portion. Alternatively and/or additionally, the side passageway can allow one or more devices (i.e. lights, cameras, medical devices, etc.) to be at least partially inserted into the interior region of the posterior end portion. Furthermore, the side passageway can be used to facilitate in guiding and/or positioning one or more implants in an intervertebral disc space. In one embodiment of the invention, one or more side passageways are positioned on at least one section of the posterior end portion. In another and/or alternative embodiment of the invention, one or more side passageways are positioned at least partially in the body portion of the insertion tool. In still another and/or alternative embodiment of the invention, one or more side passageways can have a uniform cross-sectional shape and/or size or a variable cross-sectional shape and/or size. In one aspect of this embodiment, the cross-sectional shape and/or size of at least one side passageway is substantially uniform. In another and/or alternative aspect of this embodiment, the cross-sectional shape and/or size of at least one side passageway is variable along the length of the side opening. In yet another and/or alternative embodiment of the invention, the side passageway and/or regions about the two ends of the side passageway can include one or more structures to facilitate in the positioning and/or removal of one or more devices in the side passageway, and prevent and/or allow materials to flow through and/or move into and/or out of the side passageway (e.g. valves, doors, latches, ribs, teeth, etc.). In still yet another and/or alternative embodiment of the invention, one or more side passageways includes a substantially linear passage. In a further and/or alternative embodiment of the invention, one or more side passageways include a non-linear passage. In still a further and/or alternative embodiment of the invention, the pathway of one or more side passageways is positioned substantially perpendicular to the longitudinal axis of the section of the insertion tool that includes the side passageway. In yet a further and/or alternative embodiment of the present invention, at least a portion of the pathway of one or more side passageways is not perpendicular to the longitudinal axis of the section of the insertion tool that includes the side passageway. In one aspect of this embodiment, the angle of deviation from the longitudinal axis is typically about 5–80°, more typically about 15–70°, and even more typically about 30–60°; however, other angles of deviation can be used. In still a further and/or alternative embodiment of the present invention, one end of at least one side passageway is included in the same section of the insertion tool as the other end of the same side passageway. In one aspect of this embodiment, both ends of at least one side passageway are positioned in the posterior end portion of the insertion tool. In another and/or alternative aspect of the embodiment, both ends of at least one side passageway are positioned in the body portion of the insertion tool. In still another and/or alternative aspect of this embodiment, both ends of at least one passageway are positioned in the base portion of the insertion tool. In still yet a further and/or alternative embodiment of the present invention, one end of at least one side passageway is positioned in a different section of the insertion tool of the other end of the same side passageway. In one aspect of this embodiment, one end of a side passageway is positioned in the body portion and the other end is position in the posterior end portion. In another and/or alternative aspect of this embodiment, one end of the side passageway is positioned in the body portion and the other end is positioned in the base portion. In another and/or alternative embodiment of the invention, at least one end of at least one side passageway is positioned on the inner surface of the posterior end portion, body portion, and/or base portion to facilitate in providing access to the inner region of the posterior end portion or base portion.

In another and/or alternative aspect of the present invention, the insertion tool includes one or more markings or other types of visual indicators and/or electronic indicators (e.g. markings, radiolucent material, electromagnetic transmitter, etc.) to facilitate in positioning the insertion tool in the intervertebral disc space. In one embodiment of the present invention, an insertion tool includes one or more visual markings which allows a surgeon to determine the particular position of the insertion tool in an intervertebral disc space.

In still another and/or alternative aspect of the present invention, the insertion tool includes one or more internal passageways that at least partially travel the length of the body portion and at least partially provide access to the inner region of the posterior end portion. The internal passageway can be designed, sized and/or arranged so as to achieve similar goals as the side passageway, as discussed above. The shape and/or size of the internal passageway can be selected to achieve the particular goal of the internal passageway, which are typically similar to one of the goals discussed with respect to the side passageway. In one embodiment of this invention, the inner passageway travels at least a portion of the length of the body portion and at least a portion of the length of the posterior end portion and/or base portion. In another and/or alternative embodiment of this invention, one or more openings of at least one internal passageway are positioned on the inner surface of the posterior end portion, body portion, and/or base portion to facilitate in providing access to the inner region of the posterior end portion, and/or base portion. In still yet another and/or alternative aspect of the present invention, the insertion tool can be used to clean and/or remove material from the intervertebral disc space prior to, during, and/or after an implant is inserted into the intervertebral disc space. In another and/or alternative embodiment of the present invention, one or more sections of the insertion tool can be disconnected. In one embodiment of the invention, the posterior end portion is releasably connected to the base portion. As such, various shaped and/or sized posterior end portions can be selected and connected to the body portion to perform a particular procedure on a particular patient. In another and/or alternative embodiment of the invention, the base portion is releasably connected to the body portion. As such, various shaped and/or sized base portions can be selected and connected to the body portion to perform a particular procedure on a particular patient. In still another and/or alternative embodiment of the invention, one or more regions of the posterior end portion, body portion and/or base portion are releasably connected together. In this embodiment, one or more sections of the insertion tool can be customized for a particular procedure on a particular patient. For instance, the posterior end portion can be customized to have a particular total angle of curvature and/or a particular shape. In another and/or alternative example, the length of the body portion can be extended or shortened. In still another and/or alternative example, the posterior end portion, body portion and/or base portion can be designed to have certain positioned and/or types of side passageways, internal passageways, guide mechanisms, surface profiles, and/or gripping members. In yet another and/or alternative example, the base portion can be customized to have a particular shape and/or size, a particular total angle of curvature, and/or particular gripping elements. In still yet another and/or alternative embodiment of the invention, the connection arrangement can take on many forms such as, but not limited to, threaded connections, tongue and groove connections, twist and/or snap lock connections, clamp connections, and/or the like.

In one specific non-limiting aspect of the present invention, there is provided an insertion tool and method of using an insertion tool to assist in and/or facilitate in the insertion of a medical device (e.g. prosthetic implant) into the intervertebral disc space created after all or a portion of a spinal disc is removed. The insertion tool can include a straight body section with an arcuate posterior end portion and/or arcuate base portion, and which can be hand held and/or guided mechanically or by some other method. The insertion tool can be designed to be at least partially inserted by a surgeon, into a space in a spinal column, which space has been created by the removal of all or a portion of a spinal disc, either by the surgeon or due to disease or birth defect. The insertion tool is designed to facilitate in the insertion of a prosthetic implant, to serve as a guide for such prosthetic implant, to serve as a protective barrier to ensure that the prosthetic implant being inserted does not stray beyond its intended target location, and/or to serve as a protective barrier to ensure that the prosthetic implant does not damage adjacent tissue. The prosthetic implant can be designed to facilitate in the turning and/or maneuvering and/or positioning of the prosthetic implant in an intervertebral disc space. The insertion tool can have a posterior end which is designed to have various size widths, heights, and/or thicknesses so that the surgeon can select the size insertion tool for a particular patient's needs. The insertion tool can be made of ceramic, metal, plastic, and/or bone materials which can be reusable, after sterilization, and/or disposable. The insertion tool can be a solid material with no openings or slots. The insertion tool can include one or more channels on the exterior and/or interior surface of the insertion tool, so as to permit one or more prosthetic implants or other devices to be inserted into a channel to assist in the positioning of a prosthetic implant relative to the insertion tool and/or in a proper position in the intervertebral disc space. The insertion tool can include one or more passageways which can be used to insert a light, fiber optic cable, camera, laser, and/or used as or with an irrigation system and/or suction system. Alternatively or additionally, the one or more passageways can be used to permit the introduction of medication, bone marrow, autologous growth factor, and/or other efficacious material into the inner region of the posterior end portion and/or base portion. Further and/or alternatively, the passageways can be used to insert cements, adhesives, and/or other materials which facilitate in the securing of the prosthetic implant in position in the intervertebral disc space. The insertion tool can have grooves on the exterior surface of the posterior end portion, body portion, and/or base portion which can be designed to have uses similar to the grooves as discussed above that can be positioned on the interior surface of the posterior end portion and/or base portion. The insertion tool can have a posterior end portion and/or a base portion and/or a body portion which has a substantially constant cross-sectional shape and size, and/or can have a varying cross-sectional shape and/or size. The insertion tool can be designed such that the thickness of at least a portion of the posterior end portion and/or base portion can be increased in thickness and/or reduced in thickness during a surgical procedure. The ability to increase the thickness of at least a portion of the posterior end portion and/or base portion can be used to facilitate in maintaining the spacing between two adjacent vertebrae. The reduction in thickness of at least a portion of the posterior end portion and/or base portion can be used to facilitate in inserting and/or removing the insertion tool from the intervertebral disc space. The insertion tool can be rigid, semi-rigid, or flexible depending on the desired end use of the insertion tool. The insertion tool can be used for various types of surgical procedures involving intervertebral disc spaces or other mammalian surgical procedures. The insertion tool would be particularly useful for kyphoplasty, vertebroplasty, and/or the insertion of spinal fusion cages and/or artificial discs into an intervertebral disc space. The insertion tool can have a smooth exterior surface or an unsmooth exterior surface depending on the intended end use. The insertion tool may have one or more markings to indicate measurements and/or positioning indicia on the exterior surface of the insertion tool, which markings can utilize a simple numbering or coloring systems and/or some other appropriate measuring methodology to facilitate in the positioning the insertion tool in the intervertebral disc space.

It is a principle object of the present invention to provide an insertion tool that can be used to position and/or insert one or more prosthetic implants between two vertebrae.

It is another and/or alternative object of the present invention to provide an insertion tool which minimizes or prevents damage to surrounding tissue during the use of the insertion tool.

It is yet another and/or alternative object of the present invention to provide an insertion tool which can easily and efficiently position one or more prosthetic implants between two adjacently positioned vertebrae.

It is yet another and/or alternative object of the present invention to provide an insertion tool which reduces the failure rate of prosthetic implants during a surgical procedure.

It is yet another and/or alternative object of the present invention to provide an insertion tool that is at least partially made of a biologically compatible material.

It is still another and/or alternative object of the present invention to provide an insertion tool that includes markings to enhance the visibility of the insertion tool and/or provide location and/or positioning information for the insertion tool.

It is yet another and/or alternative object of the present invention to provide an insertion tool which facilitates in the insertion of a prosthetic implant, serves as a guide for such prosthetic, serves as a protective barrier to ensure that the prosthetic implant does not stray beyond its intended location, and/or serves as a protective barrier to help ensure that the prosthetic implant does not damage adjacent tissue.

It is yet another and/or alternative object of the present invention to provide an insertion tool which includes a posterior end portion that approximates the interior curve of the intervertebral disc space into which the prosthetic implant is inserted.

It is yet another and/or alternative object of the present invention to provide an insertion tool that includes one or more gripping elements to facilitate in the positioning of the insertion tool in the intervertebral disc space.

It is still another and/or alternative object of the present invention to provide an insertion tool which includes one or more guiding arrangement used to at least partially guide and/or position one or more prosthetic implants or materials and/or devices in an intervertebral disc space.

It is still another and/or alternative object of the present invention to provide an insertion tool which includes one or more side passageways to provide access to the interior region of the posterior end portion and/or base portion from the side of the insertion tool.

It is still another and/or alternative object of the present invention to provide an insertion tool that includes one or more internal passageways which provide access to the interior region of the posterior end portion and/or base portion.

These and other objects of the invention will become apparent to those skilled in the art upon reading and understanding the following detailed description of the preferred embodiments taken together with the drawings.

BRIEF DESCRIPTION OF THE DRAWINGS

The invention may take physical form in certain parts and arrangements of parts, preferred embodiments of which will be described in detail and illustrated in the accompanying drawings which form a part hereof and wherein.

DESCRIPTION OF THE PREFERRED EMBODIMENTS

Figure 1:
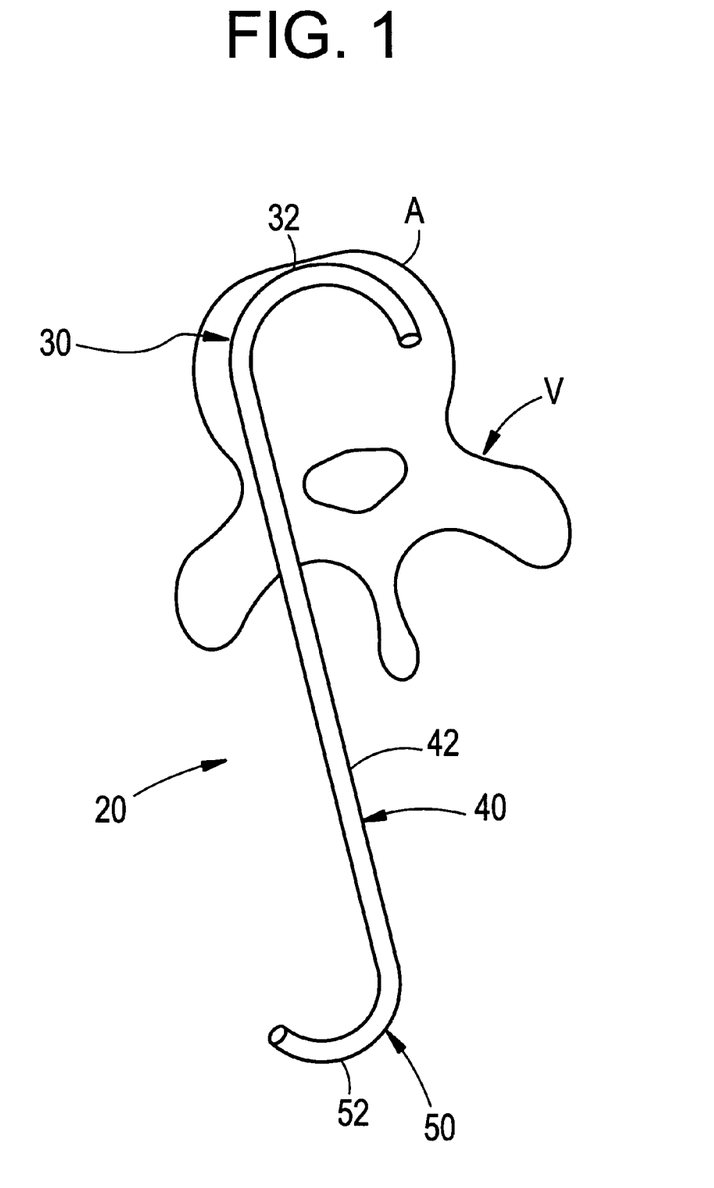
FIG. 1 is a perspective view of the insertion tool of the present invention which is positioned on the surface of a vertebrae.

Referring now to the drawings, wherein the showings are for the purpose of illustrating the preferred embodiments of the invention only and not for the purpose of limiting the same, FIG. 1 illustrates an insertion tool 20 in accordance with the present invention. Insertion tool 20 includes a posterior end portion 30 a body portion 40 and a base portion 50. As shown in FIG. 1, posterior end portion 30 is positioned within the annulus A of vertebrae V. Posterior end portion 30 has a shape such that at least a majority of the posterior end portion is positioned within the boundaries of annulus A. As shown in FIG. 1, posterior end portion 30 is sized and shaped such that all of the posterior end portion 30 is positioned within the boundaries of annulus A when insertion tool 20 is positioned in the intervertebral disc space between two adjacent vertebrae V.

Figure 2:
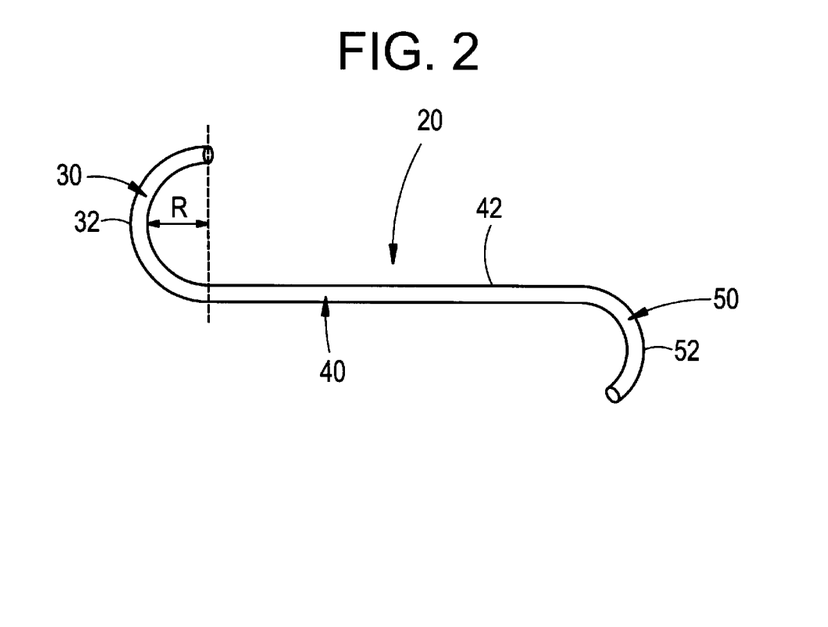
FIG. 2 is an elevation view of the insertion tool of FIG. 1.

As best illustrated in FIG. 2, posterior end portion 30 includes a radius of curvature R which is substantially constant. As can be appreciated, the radius of curvature can vary along at least a portion of the posterior end portion. The total angle of curvature of posterior end portion 30 is about 180°. As can be appreciated, the angle of curvature can be more or less than 180°. The outer surface 32 of posterior end portion 30 has a substantially smooth surface so as to minimize damage to surrounding tissue when insertion tool 20 is positioned into and out of the intervertebral disc space. The smooth surface can be formed by a coating and/or formed by sanding, polishing, and/or the like of the exterior surface. The cross-sectional shape of posterior end portion 30 is substantially uniform and has a substantially circular shape. As can be appreciated, the cross-sectional shape can be a shape other than circular, and/or the cross-sectional area of the posterior end portion can vary along one or more sections of the posterior end portion.

Posterior end portion 30 is typically formed of a durable biocompatible material that is essentially non-flexible. One such material is stainless steel, however, other types of materials can be used. As can be appreciated, one or more sections of posterior end portion 30 can be made to be flexible or semi-flexible.

As illustrated in FIGS. 1 and 2, body portion 40 is a substantially straight or linear section. Typically, the length of body portion 40 ranges between about 2–10 inches; however, other lengths can be used. The outer surface 42 of body portion 40 is substantially smooth so as to reduce the amount of damage caused by the insertion tool during the insertion and/or removal of the insertion tool from the intervertebral disc space. The cross-sectional shape and area of body portion 40 is shown to be substantially uniform along the entire length of the body portion; however, the cross-sectional shape and/or area can vary in one or more sections of the body portion. As shown in FIGS. 1 and 2, the cross-sectional shape and area of body portion 40 is substantially the same as the cross-sectional shape and area of posterior end portion 30. Typically, the material which forms body portion 40 is substantially the same as the material which forms posterior end portion 30; however, other materials can be used to form body portion 40.

Base portion 50 is illustrated as having an arcuate portion wherein the radius of curvature and the total angle of curvature is less than the radius of curvature and the total angle of curvature of posterior end portion 30. As can be appreciated, the radius of curvature and/or the total angle of curvature of base portion 50 can be the same as or greater than the radius of curvature and/or total angle of curvature of posterior end portion 30. The total angle of curvature of base portion 50 is illustrated as being less than about 180°; however, the total angle of curvature can be equal to or greater than 180°, depending on the desired shape and/or function of the base portion. The base portion is illustrated as having a substantially uniform cross-sectional shape and cross-sectional area long the entire length of the body portion; however, the cross-sectional shape and/or cross-sectional area can vary along one or more sections of the base portion. As shown in FIGS. 1 and 2, the cross-sectional shape and cross-sectional area of base portion 50 is substantially the same as the cross-sectional shape and cross-sectional area of body portion 40. Typically, the materials which form base portion 50 are substantially the same as the materials used to form body portion 40; however, the base portion can include materials which are different from the materials used to form body portion 40. The orientation of base portion 50 is such that the insertion tool has a generally S-shape; however, base portion 50 can be oriented such that the insertion tool has a generally C-shaped profile or a semi-twisted S-shaped profile. Typically, posterior end portion 30, body portion 40 and base portion 50 are formed from a single material; however, one or more portions of the insertion tool can be separately formed and subsequently connected together such as by an adhesive, thread, locking mechanism, solder, weld, and/or the like. As can be appreciated, the base portion and/or posterior end portion can be permanently or detachably connected to the body portion. If the base portion and/or posterior end portion are detachably connected to the body portion, the surgeon or another authorized personnel can select a particular shaped and/or sized and/or designed base portion and/or posterior end portion and/or body portion for use in a particular surgical procedure. Base portion 50 is typically designed so as to facilitate in the grasping of the insertion tool by a surgeon so that the insertion tool can be easily and effectively positioned into and removed from an intervertebral disc space; however, base portion 50 can have other functions, as will be described in more detail below. Typically, base portion 50 includes a generally smooth outer surface 52 so as to minimize injury or damage to the hand of the surgeon upon grasping base portion 50 when using the insertion tool in a surgical procedure.

Figure 3:
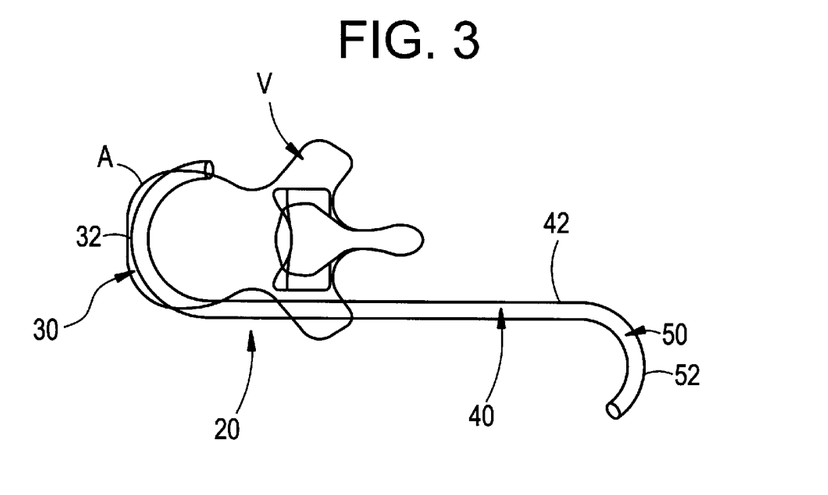
FIG. 3 is an elevation view of an alternative embodiment of the insertion tool of the present invention.

Referring now to FIG. 3, another embodiment of insertion tool 20 is illustrated. Body portion 40 and base portion 50 are designed to be essentially the same as the corresponding parts shown in FIGS. 1 and 2. Posterior end portion 30 is illustrated as having one or more sections of the posterior end portion exceeding the perimeter of the annulus A of vertebrae V. However, over a majority of posterior end portion 30 is positioned within annulus A when insertion tool 20 is inserted in the intervertebral disc space. As shown in FIG. 3, over 70% of posterior end portion 30 is positioned within the boundaries of annulus A. Typically, the posterior end portion is designed so that at least a majority of the posterior end portion is within the boundaries of annulus A.

Figure 4:
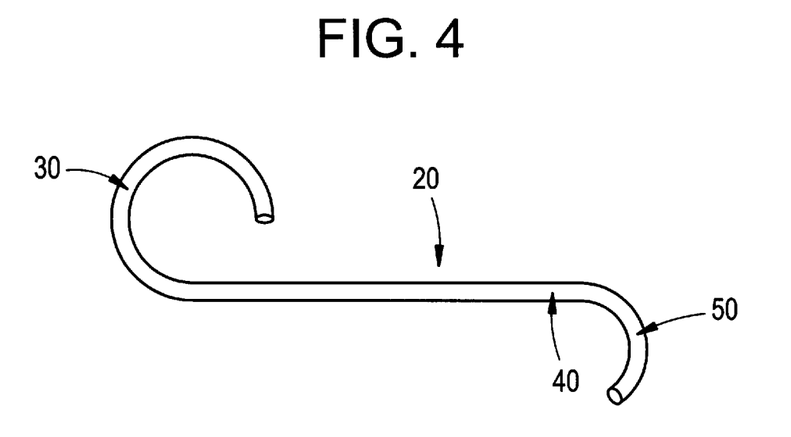
FIG. 4 is an elevation view of another alternative embodiment of the present invention.

Referring now to FIG. 4, still another embodiment of insertion tool 20 is illustrated. Body portion 40 and base portion 50 have substantially the same size and shape and perform substantially the same function as the corresponding parts as described in FIGS. 1 and 2. Posterior end portion 30 is illustrated as having a total angle or curvature which exceeds 180°. As shown in FIG. 4, the total angle of curvature of posterior end portion 30 is approximately 260°; however other angles can be used. Typically, the total angle o curvature of posterior end portion 30 does not exceed 270°. The radius of curvature of posterior end portion 30 is also illustrated as being substantially constant; however, this is not required.

Figure 5:
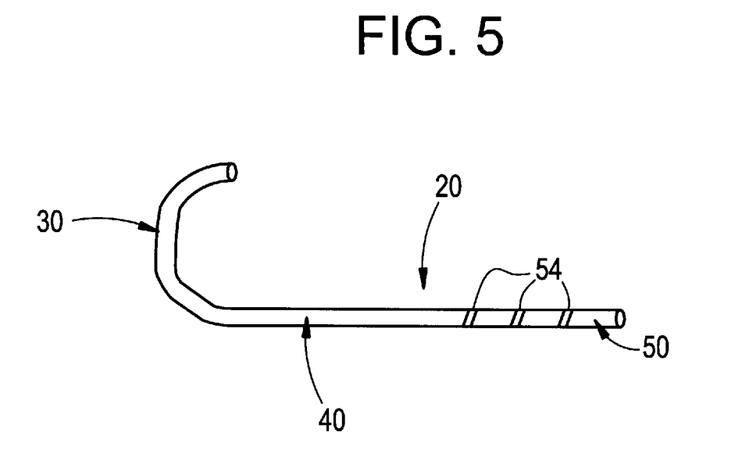
FIG. 5 is an elevation view of still another alternative embodiment of the present invention.

Referring now to FIG. 5, yet another embodiment of insertion tool 20 is illustrated. Posterior end portion 30 and body portion 40 have substantially the same size and shape and perform substantially the same function as the corresponding parts in FIGS. 1 and 2. Base portion 50 is illustrated as being substantially straight or linear. In addition, base portion 50 includes a plurality of gripping elements in the form of ribs 54. As can be appreciated, other types of gripping elements can be used. The gripping elements are formed on base portion 50 so as to facilitate in the ease of gripping and handling insertion tool 20 during a surgical procedure. As can be appreciated, gripping elements 54 can be included on a base portion 50 which includes one or more arcuate portions.

Figure 6:
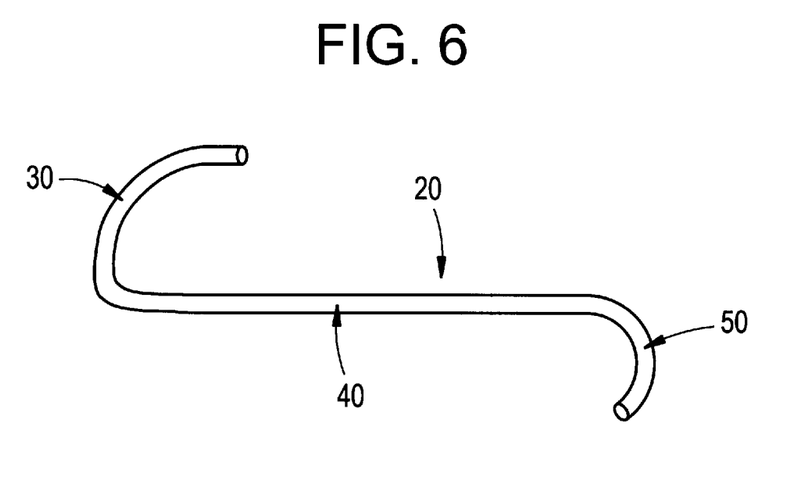
FIG. 6 is an elevation view of still yet another alternative embodiment of the present invention.

Referring now to FIG. 6, still yet another embodiment of insertion tool 20 is disclosed. Posterior end portion 30 is illustrated as having a radius of curvature which is not uniform along the length of the posterior end portion. Base portion 50 is formed so as to be used as a portion to easily grip insertion tool 20 when inserting posterior end portion 30 into an intervertebral disc space, and is also formed so that it can alternatively be used to position and/or guide one or more prosthetic implants into an intervertebral disc space. The radius of curvature of base portion 50 is illustrated as being substantially uniform; however, this is not required. In addition, the total angle of curvature of base portion 50 is illustrated as being less than 180°; however, the total angle of curvature can be equal to or greater than 180°. When base portion 50 is used to facilitate in positioning and/or orienting one or more prosthetic implants in the intervertebral disc space, posterior end portion 30 is used by the surgeon as the grasping point of the insertion tool to thereby properly maneuver and position base portion 50 within the intervertebral disc space. When both the base portion 50 and posterior end portion 30 are designed to be used for positioning one or more prosthetic implants in an intervertebral disc space, the materials which form the base portion 50 and posterior end portion 30 are generally the same. In addition, the radius of curvature and/or the total angle of curvature of base portion 50 is typically different from the radius of curvature and/or the total angle of curvature of posterior end portion 30. As a result, insertion tool 20 has two distinct ends which can be used in the same and/or different intervertebral disc spaces during a surgical procedure, thus increasing the versatility of the insertion tool 20. Furthermore, base portion 50 and posterior end portion 30 typically have substantially smooth surfaces so as not to damage surrounding tissue when the base portion 50 and/or posterior end portion 30 is inserted into an intervertebral disc space. Body portion 40 has substantially the same shape and cross-sectional area and performs substantially the same function as the corresponding parts as disclosed in FIGS. 1 and 2.

Figure 7:
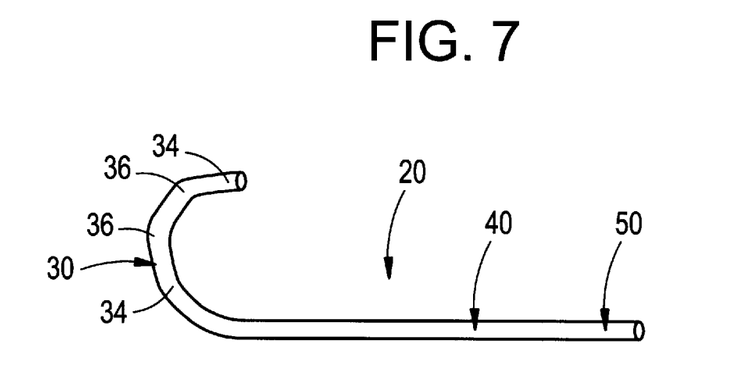
FIG. 7 is an elevation view of a further alternative embodiment of the insertion tool of the present invention.

Referring now to FIG. 7, still yet another alternative embodiment of the insertion tool 20 is disclosed. Posterior end portion 30 is illustrated as including a plurality of straight sections 34 and a plurality of arcuate sections 36. As can be appreciated, posterior end portion 30 can include a single straight portion 30 and/or a single arcuate portion 36. The radius of curvature of posterior end portion 30 is not constant due to the use of straight sections and arcuate sections to form the posterior end portion. The total angle of curvature of posterior end portion is illustrated as being approximately 180°; however, the angle of curvature can be less than or greater than 180°. Base portion 50 is illustrated as being substantially straight; however, as indicated above, base portion 50 can be arcuate shaped and/or include one or more gripping elements.

Figure 8:
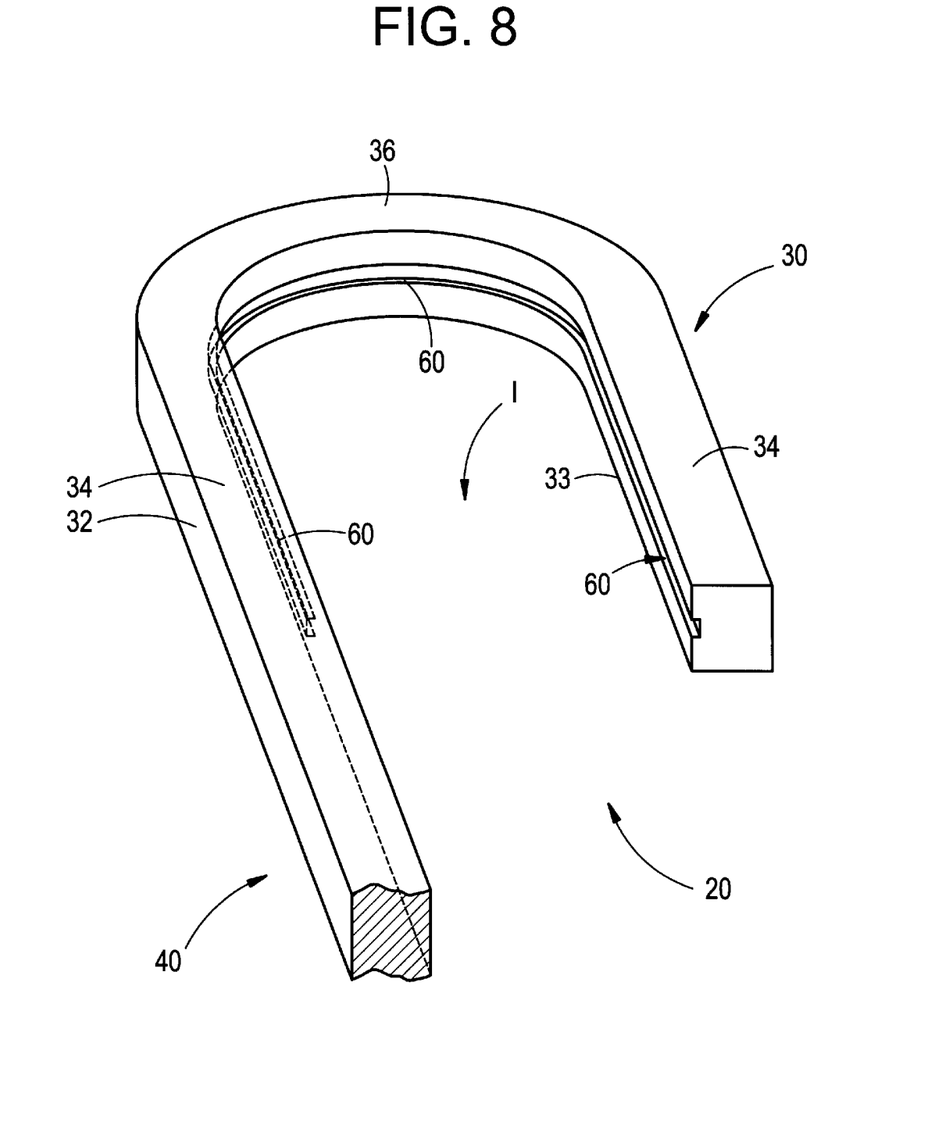
FIG. 8 is an enlarged sectional view of a portion of the insertion tool of the present invention illustrating a groove positioned in the inner surface of the posterior end portion.

Referring now to FIG. 8, a further alternative embodiment of the insertion tool is disclosed. FIG. 8 illustrates an enlarged sectional view of the insertion tool that includes posterior end portion 30 and a section of body portion 40. As illustrated in FIG. 8, the cross-sectional shape of posterior end portion 30 and body portion 40 are substantially square; however, other shapes can be used. Posterior end portion 30 is also illustrated as including two straight sections 34 and a single arcuate section 36. The radius of curvature of the arcuate section 36 is substantially constant; however, this is not required. The total angle of curvature of posterior end portion 30 is illustrated as being approximately 180°; however, the total angle of curvature can be greater or less than 180°. The inner surface 33 of posterior end portion 30 is illustrated as including a groove 60. Groove 60 is illustrated as having the same size and/or shape along its length; however, this is not required. Groove 60 is also illustrated as extending along the total inner surface 33 of posterior end portion 30; however, this is not required. Furthermore, groove 60 is illustrated as being positioned in the center of inner surface 33 along the length of the groove; however, this is not required. Groove 60 is adapted to function as a guiding mechanism for guiding one or more prosthetic implants within interior region I of posterior end portion 30. Alternatively and/or additionally, groove 60 can be used to guide and/or position other materials and/or devices into interior region I. When one or more prosthetic implants, materials, and/or devices are to be guided by groove 60, such prosthetic implants, materials, and/or devices typically include a corresponding structure designed to coact with groove 60 so as to be at least partially guided and/or positioned by the groove within interior region I of posterior end portion 30. As can be appreciated, other guiding mechanisms can be used such as a ribbed configuration, a track and/or the like.

Figure 9:
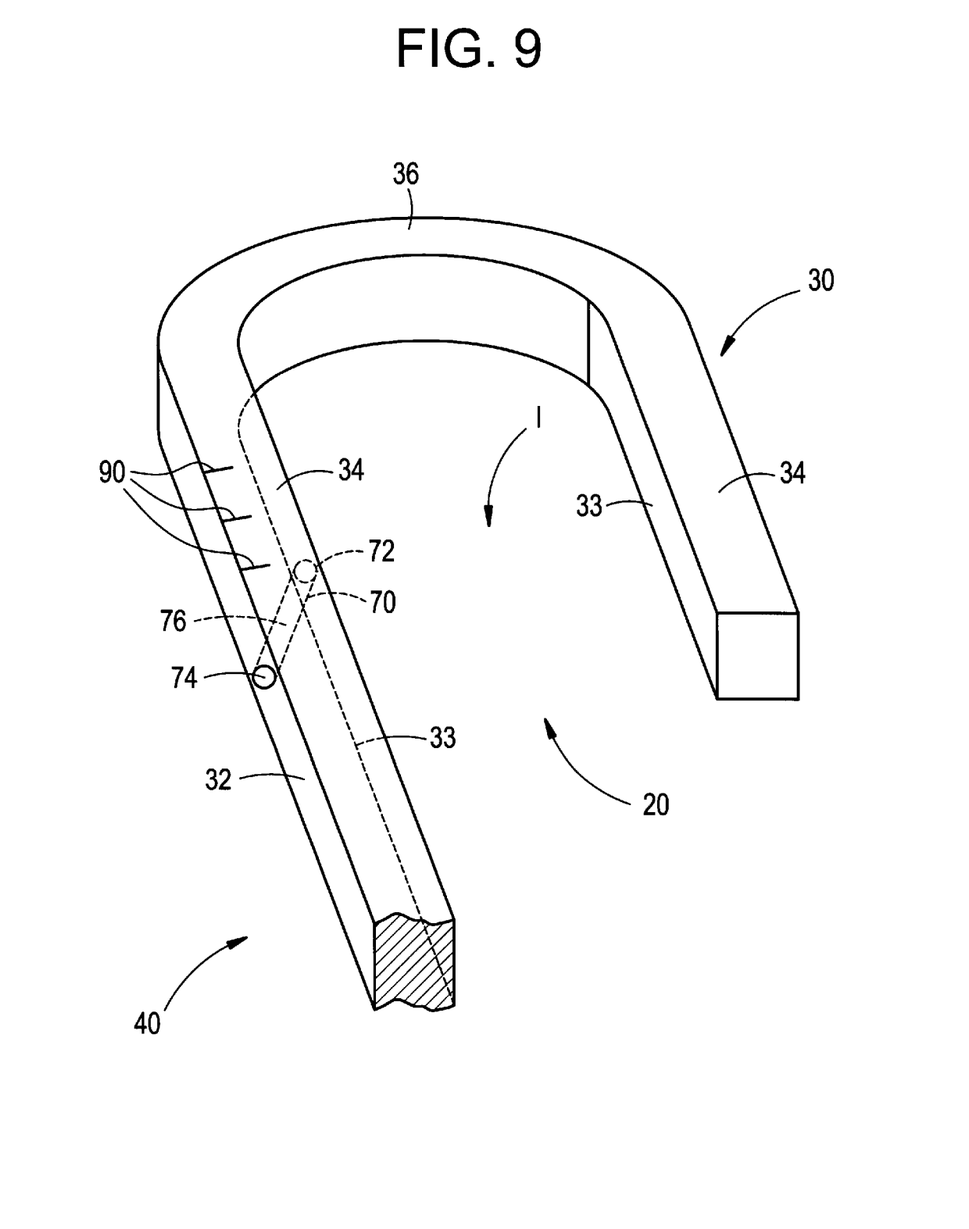
FIG. 9 is an enlarged sectional view of the insertion tool of the present invention which illustrates a side passageway in a portion of the insertion tool; and, FIG. 10 is an enlarged sectional view of the insertion tool of the present invention illustrating an internal passageway in at least a portion of the insertion tool of the present invention.

Referring now to FIG. 9, yet a further or alternative embodiment of insertion tool 20 is illustrated. Posterior end portion 30 is formed by two straight sections 34 and a single arcuate section 36, which is similar to FIG. 8. The structures and orientations of these sections is similar to the corresponding structures discussed above with respect to FIG. 8. At least one of straight sections 34 includes one or more markings 90. These markings can be colored markings, etched markings, or some other type of visual markings which facilitate in informing the surgeon the position of the insertion tool relative to the intervertebral disc space or other region around the surgical site. The markings are illustrated as being on the top surface of posterior end portion 30; however, the markings can be in other locations on the posterior end portion and/or located on body portion 40. One of the legs of one of the straight sections 34 of posterior end portion 30 also includes a side passageway 70. The side passageway includes an access opening 72 on interior surface 33 and an access opening 74 on exterior surface 32. A channel 76 is connected between access openings 72 and 74. Openings 72 and 74 are illustrated as being substantially circular and having substantially the same cross-sectional area; however, the access openings can have shapes other than a circular shape and/or can have different size cross-sectional areas. Channel 76 is illustrated as being a substantially cylindrically shaped passageway; however, other shaped and sized passageways can be used. Side passageway 70 is designed to provide access from the side of insertion tool 20 into interior region I during a surgical procedure. The side passageway can be used to insert and/or remove materials from the interior region I and/or insert and/or remove one or more devices (e.g. camera, light, medical device, etc.). As can be appreciated, posterior end portion 30 can include more than one side passageway. In addition, the body portion of the insertion tool can include one or more side passageway. As illustrated in FIG. 9, side opening 70 is positioned at an approximately 45° angle relative to the longitudinal axis of straight section 34. As can be appreciated, side passageway 70 can be oriented at other angles (e.g. between 0-90°) relative to the longitudinal axis.

Figure 10:
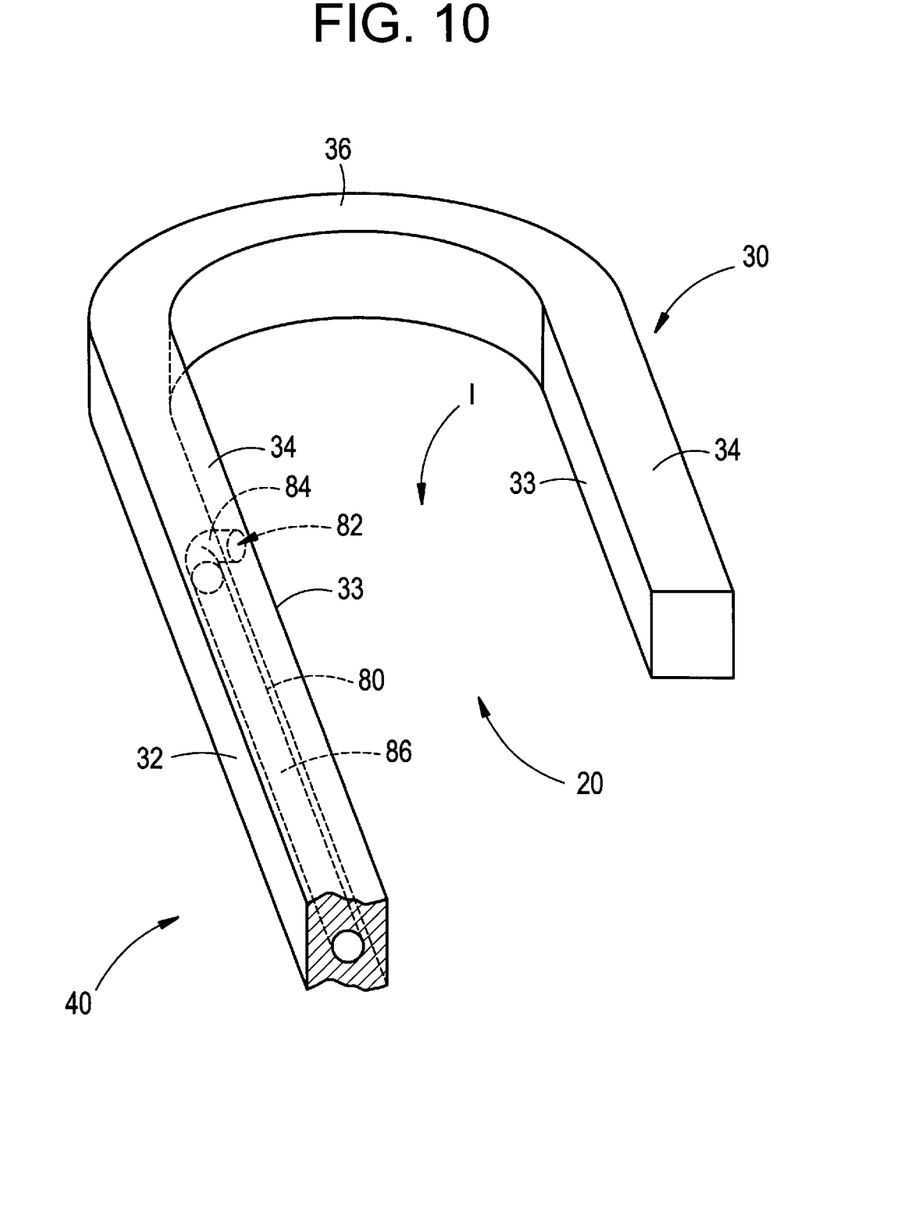

Referring now to FIG. 10, still another alternative embodiment of the insertion tool 20 is illustrated. FIG. 10 illustrates an enlarged sectional view of posterior end portion 30 and a portion of body portion 40 which has a similar cross-sectional shape and orientation as the corresponding parts illustrated in FIGS. 8 and 9. An internal passageway 80 is shown as running along at least a portion of the longitudinal length of body portion 40 and into at least a portion of posterior end portion 30. Internal passageway 80 can be designed to run the full length or partial length of body portion 40. In addition, internal passageway 80 can be designed to run fully through the body portion and/or at least partially run through base portion 50, which is not shown. Internal passageway 80 is shown to include a substantially cylindrically shaped corridor 86. As can be appreciated, corridor 86 can have shapes other than a cylindrical shape and does not necessarily have to be a substantially straight corridor, and can further vary in cross-sectional area along the length of the corridor. As illustrated in FIG. 10, corridor 86 converges with passageway 84, which exits into side portal opening 82. Side portal 82 is illustrated as being a substantially circular shaped portal; however, other shapes can be used. In FIG. 10, a single portal opening is illustrated; however, as can be appreciated, posterior end portion 30 can include more than one portal opening, and such portal opening can be positioned anywhere along the interior surface 33 of posterior end portion 30. In addition, it can be appreciated that one or more portal openings can be located on the interior surface of body portion 40. Internal channel 80 can be used for similar reasons as side passageway 70, as discussed with respect to FIG. 9.

The insertion tool as described above can be used for inserting one or more prosthetic implants from the interior, posterior, and lateral aspect of the spine. As stated above, the insertion tool provides protection to the surrounding tissue, as it acts as a protective barrier to delicate soft tissue structures, nerves, blood vessels, and organs outside the path of the various sharp surgical instruments used when inserting one or more implants and from the implant itself. The insertion tool can also be used in the surgical site to protect against debris generated during one or more surgical procedures and/or can be used in conjunction with other procedures to insert and/or remove various fluids or materials from a surgical site during a surgical procedure. In essence, the insertion tool facilitates in ensuring that one or more prosthetic implants are successfully placed and/or positioned in an intervertebral disc space.

The method of the present invention typically includes positioning a patient on a spinal surgery frame which allows for the distraction and alignment of the disc space to be surgically acted on. Typically, a bilateral posterior exposure of the inner space, with or without partial discectomy is performed. Distractors are used in the intervertebral disc space to partially or fully remove the intervertebral disc. The bone of the vertebrae is typically prepared by grinding to expose fresh bone which facilitates in the fusion of the spinal implant with the vertebrae. Thereafter, one or more prosthetic implants are inserted into the intervertebral disc space to allow the fusion to occur between the vertebrae and the one or more prosthetic implants. During the surgical procedure, the adjacent vertebrae which form the intervertebral disc space can be separated and/or maintained in position during a surgical procedure. The insertion tool of the present invention is typically utilized after the disc has been fully or partially removed. Typically, an insertion tool is selected such that the posterior end portion has a shape such that all of the posterior end portion remains within the boundaries of the annulus of the vertebrae. Typically, the cross-sectional area of the posterior end portion of the insertion tool is sized and selected so that such cross-sectional shape has a maximum thickness which is less than or equal to the minimum thickness of the intervertebral disc space being operated on. Such a selection of the insertion tool allows the insertion tool to be easily inserted into, maneuvered, and removed from the surgical site during the surgical procedure. The insertion tool can be positioned in the annulus in the intervertebral disc space prior to or after the bone on the vertebrae has been partially ground down to expose the fresh tissue, if such grinding is to be performed. If the insertion tool is positioned in the intervertebral disc space prior to the grinding procedure, if one is used, the posterior end portion of the insertion tool acts as a partial barrier which inhibits or prevents bone shavings from migrating away from the surgical site. The insertion tool can include one or more side passageways or one or more internal canals which can be used to flush out a site and/or clean a site during such a procedure. Alternatively and/or additionally, one or more side passages or internal passageways can include a light or camera which allows a surgeon to better visually view the surgical site during the procedure. After the bones of the vertebrae has been properly prepared and spaced apart, one or more prosthetic implants are inserted into the intervertebral disc space. The posterior end portion of the insertion tool acts as a barrier so as to limit or prevent damage to surrounding tissue during the insertion of the one or more prosthetic implants. The insertion tool can include one or more guiding arrangements which can be used to at least partially guide the one or more prosthetic implants into the proper position in the intervertebral disc space. Once the one or more prosthetic implants are properly positioned, the surgical site can be further treated by applying medicine, bone growth factors, cements, adhesives, and/or other substances into the intervertebral disc space, which substances are used to help promote a successful surgical procedure. These one or more substances can be inserted into the desired site by the use of the one or more side passages or internal passageways of the insertion tool. After the one or more prosthetic implants have been positioned and the surgical site has been properly treated, the insertion tool is removed from the intervertebral disc space.

The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

I claim:

1. An insertion tool to at least partially guide or insert an implant into an intervertebral disc space comprising a body portion and a curvilinear top portion connected to a first end of said body portion and a lower portion connected to a second end of said body portion, said lower portion having a cumulative angle of curvature of over 45°, said curvilinear top portion having a cumulative angle of curvature of at least about 90°, a majority of a bottom surface of said top and lower portion substantially lie in the same plane.

2. The tool as defined in claim 1, wherein a majority of said body portion is substantially linear.

3. The tool as defined in claim 1, wherein at least a portion of said body portion has a cross-sectional shape selected from the group consisting of circular, rectangle, oval, and square.

4. The tool as defined in claim 1, wherein said cumulative angle of curvature of said top portion is at least about 135°.

5. The tool as defined in claim 1, wherein said cumulative angle of curvature of said top portion is at least about 180°.

6. The tool as defined in claim 1, wherein a majority of said top portion has a constant radius of curvature.

7. The tools as defined in claim 1, wherein at least a portion of said top portion has a cross-sectional shape selected from the group consisting of circular, rectangular, oval, and square.

8. The tool as defined in claim 1, wherein a majority of a bottom surface of said top portion substantially lies in the same plane.

9. The tool as defined in claim 1, wherein said top portion has a size and shape such that over 50% of said top portion can be positioned within an outer perimeter of said intervertebral disc space.

10. The tool as defined in claim 1, wherein said top portion has a size and shape such that over 80% of said top portion can be positioned within an outer perimeter of said intervertebral disc space.

11. The tool as defined in claim 1, wherein said body portion includes at least one gripping element.

12. The tool as defined in claim 1, wherein said top portion includes a guide slot.

13. The tool as defined in claim 1, wherein said body portion includes a guide slot.

14. The tool as defined in claim 1, wherein said top portion includes at least one positioning marker.

15. The tool as defined in claim 1, wherein said body portion includes at least one positioning marker.

16. The tool as defined in claim 1, wherein said top portion includes a side opening.

17. The tool as defined in claim 1, wherein said top portion includes an inner channel.

18. The tool as defined in claim 1, wherein said body portion includes an inner channel.

19. The tool as defined in claim 1, wherein said lower portion has a cumulative angle of curvature of over 90°.

20. The tool as defined in claim 1, wherein a majority of said lower portion has a constant radius of curvature.

21. The tools as defined in claim 1, wherein at least a portion of said lower portion has a cross-sectional shape selected from the group consisting of circular, rectangular, oval, and square.

22. The tool as defined in claim 1, wherein a majority of a bottom surface of said lower portion substantially lies in the same plane.

23. The tool as defined in claim 1, wherein said lower portion has a size and shape such that over 50% of said lower portion can be positioned within an outer perimeter of said intervertebral disc space.

24. A method of at least partially guiding or inserting an implant into an intervertebral disc space comprising:
   a. at least partially inserting an insertion tool into an intervertebral disc space, said insertion tool including an extended body portion and a curvilinear top portion connected to a first end of said body portion and a lower portion connected to a second end of said body portion, said lower portion having a cumulative angle of curvature of over 45°, said top portion having a cumulative angle of curvature of at least about 90°, a majority of a bottom surface of said top and lower portion substantially lie in the same plane;
   b. positioning said top portion in said intervertebral disc space until over 50% of said top portion is positioned within an outer perimeter of said disc space;
   c. positioning at least one implant at least partially in said intervertebral disc space;
   d. using said top portion of said insertion tool to at least partially protect tissue surrounding said intervertebral disc space from being damaged by said implant during insertion and/or positioning said implant in said intervertebral disc space; and,
   e. removing said insertion tool from said intervertebral disc space.

25. An insertion tool to at least partially guide or insert an implant into an intervertebral disc space comprising a body portion, a curvilinear top portion, and a lower portion, said body portion having an anterior and posterior end, said curvilinear top portion having a first end and a second end and having a cumulative angle of curvature from the first end to the second end of over 90°, said first end of said curvilinear top portion connected to the anterior end of said body portion, said lower portion having a first end and a second end, said first end of said lower portion connected to the posterior end of said body portion, said lower portion having a cumulative angle of curvature from said first end to said second end of over 45°.

26. The tool as defined in claim 25, wherein said cumulative angle of curvature of said top portion is at least about 135°.

27. The tool as defined in claim 25, wherein said lower portion has a cumulative angle of curvature of over 90°.

28. The tool as defined in claim 25, wherein said cumulative angle of curvature of said top portion is at least about 135°.

29. The tool as defined in claim 28, wherein said body portion, top portion and lower portion form a generally "S" shape.

30. The tool as defined in claim 25, wherein said top portion is substantially "U" shaped.

31. The tool as defined in claim 30, wherein said lower portion is substantially "U" shaped.

32. The tool as defined in claim 31, wherein a majority of said body portion is substantially linear.

33. The tool as defined in claim 32, wherein said top portion has a size and shape such that over 50% of said top portion can be positioned within an outer perimeter of said intervertebral disc space.

34. The tool as defined in claim 33, wherein said top portion has a size and shape such that over 80% of said top portion can be positioned within an outer perimeter of said intervertebral disc space.

35. The tool as defined in claim 34, wherein said lower portion has a size and shape such that over 50% of said lower portion can be positioned within an outer perimeter of said intervertebral disc space.

36. The tool as defined in claim 25, wherein said lower portion has a size and shape such that over 80% of said lower portion can be positioned within an outer perimeter of said intervertebral disc space.

37. The tool as defined in claim 36, wherein a majority of a bottom surface of said top an lower portion substantially lie in the same plane.

38. The tool as defined in claim 37, wherein said body portion includes at least one gripping element.

39. The tool as defined in claim 38, wherein said top portion includes a guide slot positioned along at least a majority of the length of said top portion.

40. The tool as defined in claim 39, wherein said body portion includes a guide slot.

41. The tool as defined in claim 25, wherein said body portion, top portion and lower portion form a generally "S" shape.

42. The tool as defined in clam 25, wherein said top portion is substantially "U" shaped.

43. The tool as defined in claim 25, wherein said lower portion is substantially "U" shaped.

44. The tool as defined in claim 25, wherein a majority of said body portion is substantially linear.

45. The tool as defined in claim 25, wherein said top portion has a size and shape such that over 50% of said top portion can be positioned within an outer perimeter of said intervertebral disc space.

46. The tool as defined in claim 45, wherein said top portion has a size and shape such that over 80% of said top portion can be positioned within an outer perimeter of said intervertebral disc space.

47. The tool as defined in claim 25, wherein said lower portion has a size and shape such that over 50% of said lower portion can be positioned within an outer perimeter of said intervertebral disc space.

48. The tool as defined in claim 47, wherein said lower portion has a size and shape such that over 80% of said lower portion can be positioned within an outer perimeter of said intervertebral disc space.

49. The tool as defined in claim 25, wherein a majority of a bottom surface of said top and lower portion substantially lie in the same plane.

50. The tool as defined in claim 25, wherein said body portion includes at least one gripping element.

51. The tool as defined in claim 25, wherein said top portion includes a guide slot positioned along at least a majority of the length of said top portion.

52. The tool as defined in claim 51, wherein said body portion includes a guide slot.

53. The tool as defined in claim 25, wherein said top portion includes at least one positioning marker.

54. The tool as defined in claim 53, wherein said body portion includes at least on positioning marker.

55. The tool as defined in claim 25, wherein said body portion includes at least one positioning marker.

56. The tool as defined in claim 25, wherein said top portion includes a side opening and an inner channel connected to said side opening.

57. The tool as defined in claim 56, wherein said body portion includes a side opening and an inner channel, said inner channel of said body portion connected to said inner channel in said top portion.

58. The tool as defined in claim 25, wherein said body portion includes a side opening and an inner channel.

59. A method of at least partially guiding or inserting an implant into an intervertebral disc space comprising:

a. at least partially inserting an insertion tool into an intervertebral disc space, said insertion tool including a body portion and a curvilinear top portion, said body portion having an anterior and posterior end, said curvilinear top portion having a first end and a second end and having a cumulative angle of curvature from the first end to the second end of over 90°, said first end of said curvilinear top portion connected to the anterior end of said body portion;

b. positioning said top portion in said intervertebral disc space until over 50% of said top portion is positioned within an outer perimeter of said disc space;

c. positioning at least one implant at least partially in said intervertebral disc space;

d. using said top portion of said insertion tool to at least partially protect tissue surrounding said intervertebral disc space from being damaged by said implant during insertion and/or positioning said implant in said intervertebral disc space; and, e. removing said insertion tool from said intervertebral disc space.

60. The method as defined in claim 59, wherein said insertion tool includes a lower portion having a first end and a second end, said first end of said lower portion connected to the posterior end of said body portion, said lower portion having a cumulative angle of curvature from said first end to said second end of over 45°.

61. The method as defined in claim 60, wherein said body portion, top portion and lower portion form a generally "S" shape.

62. The method as defined in claim 61, wherein said top portion is substantially "U" shaped.

63. The method as defined in claim 60, wherein said lower portion is substantially "U" shaped.

64. The method as defined in claim 59, wherein a majority of a bottom surface of said top and lower portion substantially lie in the same plane.

65. The method as defined in claim 59, wherein said body portion includes at least one gripping element.

66. The method as defined in claim 59, wherein said top portion includes a guide slot positioned along at least a majority of the length of said top portion.

67. The method as defined in claim 59, wherein said body portion includes a guide slot.

68. The method as defined in claim 59, wherein said top portion includes at least one positioning marker.

69. The tool as defined in claim 59, wherein said top portion includes a side opening and an inner channel connected to said side opening.

70. The tool as defined in claim 59, wherein said body portion includes a side opening and an inner channel, said inner channel of said body portion connected to said inner channel in said top portion.

* * * * *